(12) United States Patent
Knox

(10) Patent No.: US 6,758,840 B2
(45) Date of Patent: Jul. 6, 2004

(54) DRUG DELIVERY DEVICE

(75) Inventor: Peter Knox, Berkshire (GB)

(73) Assignee: Metris Therapeutics Limited, Wokingham (GB)

( * ) Notice: Subject to any disclaimer, the term of this patent is extended or adjusted under 35 U.S.C. 154(b) by 243 days.

(21) Appl. No.: 09/840,004

(22) Filed: Apr. 20, 2001

(65) Prior Publication Data

US 2002/0022816 A1 Feb. 21, 2002

(30) Foreign Application Priority Data

Apr. 20, 2000 (GB) .............................................. 0009914

(51) Int. Cl.[7] .............................................. A61F 13/20
(52) U.S. Cl. .......................... 604/385.18; 604/385.17; 604/904; 604/514; 424/731
(58) Field of Search ................. 604/514, 575, 604/385.17, 385.18, 904; 424/76.1–76.7, 731

(56) References Cited

U.S. PATENT DOCUMENTS

| | | | |
|---|---|---|---|
| 2,739,593 A | 3/1956 | McLaughlin | |
| 3,521,637 A | 7/1970 | Waterbury et al. | ........... 128/270 |
| 3,545,439 A | 12/1970 | Duncan | ........... 128/260 |
| 3,884,233 A | * 5/1975 | Summey | ........... 604/15 |
| 3,902,493 A | 9/1975 | Baier et al. | ........... 128/270 |
| 3,918,452 A | 11/1975 | Cornfield | ........... 128/270 |
| 3,948,265 A | 4/1976 | Al Ani | ........... 128/267 |

(List continued on next page.)

FOREIGN PATENT DOCUMENTS

| | | | | |
|---|---|---|---|---|
| DE | 1 581 474 | 4/1977 | ........... | A61M/31/00 |
| DE | 3327086 | 2/1984 | | |
| EP | 0 129 271 | 9/1987 | ............ | A61F/5/46 |
| EP | 0 418 642 B1 | 6/1993 | ........... | A61K/37/30 |
| EP | 0 703 802 B1 | 3/1999 | ........... | A61M/31/00 |
| GB | 1480615 | 7/1977 | | |
| GB | 2069336 B | 8/1981 | ............ | A61K/9/00 |
| GB | 2153686 B | 7/1987 | ............ | A61F/5/46 |
| GB | 2 311 726 A | 10/1997 | | |
| WO | WO 86/01998 | 4/1986 | ............ | A61F/5/46 |
| WO | WO 98/56323 | 12/1998 | ............ | A61F/6/06 |
| WO | WO 99/18884 | 4/1999 | ............ | A61D/7/00 |
| WO | WO 99/24085 | 5/1999 | | |
| WO | WO 99/26556 | 6/1999 | ........... | A61D/19/00 |
| WO | WO 99/40966 | 8/1999 | ........... | A61M/31/00 |
| WO | WO 99/56724 | 11/1999 | ........... | A61K/99/00 |
| WO | WO 99/63967 | 12/1999 | ............ | A61K/9/00 |
| WO | WO 00/48539 | 8/2000 | ............ | A61F/6/06 |

OTHER PUBLICATIONS

Kullander, S. et al., Acta Obstet. Gynecol. Scand., On Resorption and the Effects of Vaginally Administered Terbutaline in Women with Premature Labor, (1985), 64, 613–616.

Moodley, J. et al., S. Afr. Med. J., Vaginal absorption of low–dose tranexamic acid from impregnated tampons, (1992), 81, 150–152.

Igarashi, M., Asia Oceania J. Obstet. Gynaecol., A New Therapy for Pelvic Endometriosis and Uterine Adenomyosis: Local Effect of Vaginal and Intrauterine Danazol Application, (1990), 16, 1–12.

*Primary Examiner*—John J. Calvert
*Assistant Examiner*—Jacqueline F Stephens
(74) *Attorney, Agent, or Firm*—Klauber & Jackson

(57) ABSTRACT

The invention relates to drug delivery devices for insertion into the vagina, rectum or nasal cavity comprising a body, a layer of fluid-impermeable material on at least part of said body and one or more pharmaceutical agents disposed on the surface of the material remote from said body, wherein said body comprises absorbent material. The devices exploit the highly vascularised nature of the vaginal, nasal and rectal mucosal tissue to deliver pharmaceutical agents to localised areas and/or into underlying tissues.

23 Claims, 6 Drawing Sheets

U.S. PATENT DOCUMENTS

| | | |
|---|---|---|
| 4,286,596 A | 9/1981 | Rubinstein .................. 128/270 |
| 4,308,867 A | 1/1982 | Roseman et al. |
| 4,318,405 A | 3/1982 | Sneider ....................... 128/263 |
| 4,340,055 A | 7/1982 | Sneider ....................... 128/270 |
| 4,402,693 A | 9/1983 | Roseman et al. ........... 604/890 |
| 4,564,362 A | 1/1986 | Burnhill ..................... 604/286 |
| 4,601,714 A | 7/1986 | Burnhill ..................... 604/286 |
| 5,002,540 A | 3/1991 | Brodman et al. |
| 5,269,321 A | 12/1993 | MacDonald et al. |
| 5,273,521 A | 12/1993 | Peiler et al. .................. 604/13 |
| 5,299,581 A | 4/1994 | Donnell et al. ............. 128/830 |
| 5,409,955 A | 4/1995 | Bockow et al. ............. 514/560 |
| 5,527,534 A | 6/1996 | Myhling ..................... 424/430 |
| 5,543,150 A | 8/1996 | Bologna et al. |
| 5,612,045 A | 3/1997 | Syverson |
| 5,694,947 A | 12/1997 | Lehtinen et al. ............ 128/833 |
| 5,766,632 A | 6/1998 | Oldham et al. ............. 424/486 |
| 5,840,771 A | 11/1998 | Oldham et al. ............. 514/931 |
| 5,846,216 A | 12/1998 | Gonzales et al. ............... 604/2 |
| 5,912,006 A | 6/1999 | Bockow et al. ............. 424/431 |
| 5,954,688 A | 9/1999 | Adams et al. ................. 604/59 |
| 6,066,338 A | 5/2000 | Oldham et al. ............. 424/486 |
| 6,074,671 A | 6/2000 | Oldham et al. ............. 424/486 |
| 6,086,909 A | 7/2000 | Harrison et al. ............ 424/430 |
| 6,103,256 A | 8/2000 | Nabahi ....................... 424/430 |
| 6,159,174 A | 12/2000 | Oldham et al. ............... 602/77 |
| 6,197,327 B1 | 3/2001 | Harrison et al. ............ 424/430 |

\* cited by examiner

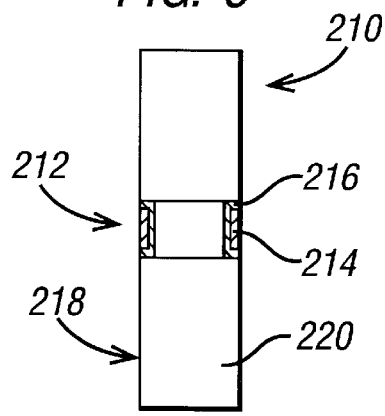
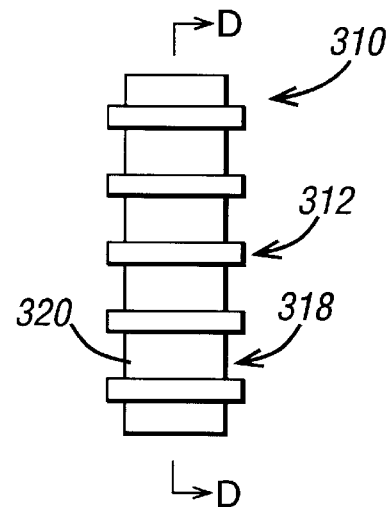
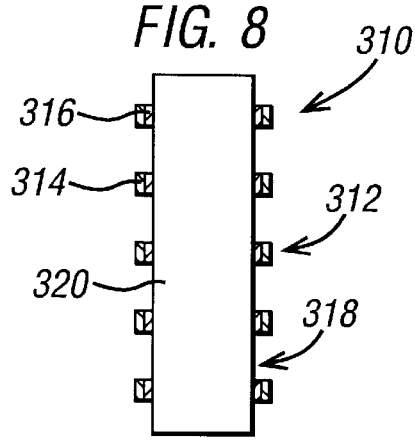
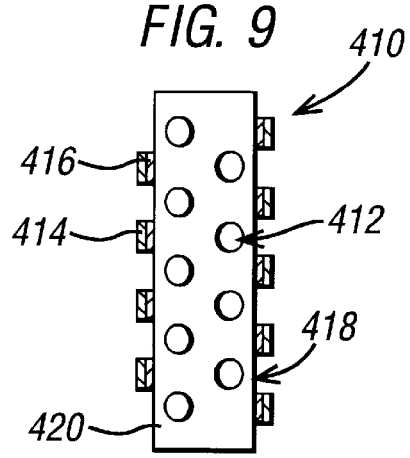
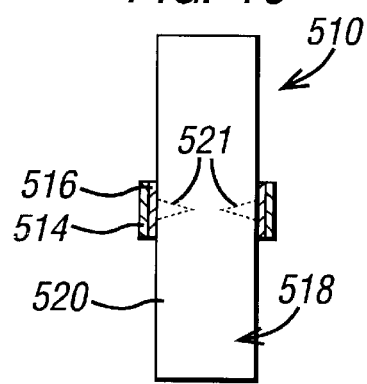
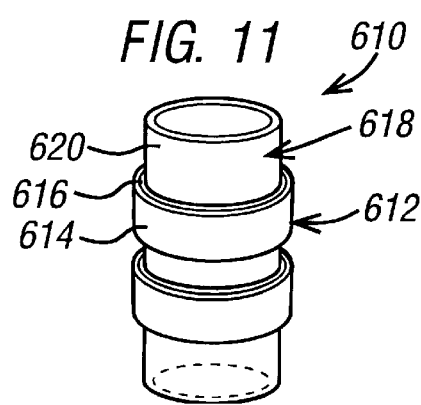

Tampon #1   Tampon #2   Tampon #3

With impermeable layer

Without impermeable layer

DRUG DELIVERY DEVICE

This invention concerns drug delivery devices for insertion into the vagina, rectum or nasal cavity. The devices exploit the highly vascularised nature of the vaginal, nasal and rectal mucosal tissue to deliver pharmaceutical agents to localised areas and/or into underlying tissues.

The vagina, rectum and nasal cavity provide an excellent route for the administration of pharmaceutical agents due to the copious blood supply in these regions. Delivery of the agent through the tissue wall is generally fast. Any one of vaginal, rectal and nasal administration can be a preferred route when drug can be destroyed by local conditions such as those encountered in the stomach. Other very important situations when the oral route is precluded are when vomiting has occurred, or is likely to occur, when the patient is unable to swallow successfully and when the patient is unconscious.

The vaginal delivery route is known to be useful for the delivery of pharmaceutical agents which have their site of action within tissues or organs close to the vagina, in particular, for administration to the vaginal tissues, uterus, ovaries and Fallopian tubes and other tissues and organs within the peritoneal cavity. Pathological lesions within and around these organs may also be treated in this manner.

The vagina may also be used for the delivery of pharmaceutical agents intended for use in other regions of the body. Administration through the vaginal cavity is particularly useful where other formulations are unsuitable, for example, in situations where pharmaceutical agents aggravate or upset the stomach, or are difficult or impossible to administer orally. Such agents may conveniently be administered intra-vaginally.

Intra-vaginal devices for the delivery of pharmaceutical agents and other materials into the vaginal cavity are known. Such devices are either of the type where a medicament is impregnated into the device, or of the type that carries an encapsulated medicament.

For example, U.S. Pat. No. 4,309,997 discloses a moist, medicated vaginal tampon that is impregnated with a contraceptive agent and a medicament for the control of venereal disease.

U.S. Pat. No. 4,318,405 discloses a tampon which has a capsule of disintegratable material partially embedded in one end. This tampon is inserted into the vagina and serves both to deliver and to retain the encapsulated medicament in the vaginal cavity. This patent also discloses a means for prewetting the tampon in order to activate the capsule.

U.S. Pat. No. 5,527,534 discloses a sponge, impregnated with a liquid containing an effective amount of an active pharmaceutical agent, for insertion into the vaginal cavity.

U.S. Pat. No. 5,273,521 discloses a tampon assembly that is adapted for carrying a medicament within a longitudinal bore formed within the tampon. The medicament can be selectively expelled into the vaginal cavity from the bore using a tubular inserter.

One disadvantage of the intra-vaginal devices described above is that, where the tampon or sponge comprises an absorbent material, it will itself absorb much of the pharmaceutical agent. On the other hand, where the intra-vaginal device comprises non-absorbent material, or is saturated with a medicament, then the natural tendency of the vaginal cavity to flush fluid away will result in the expulsion of much of the medicament from the vagina, particularly during menstruation.

Movement of pharmaceutical molecules from the vaginal cavity into the surrounding tissues is usually via a simple diffusion process. Net diffusion may be given by the equation:

$$\text{Net diffusion} = k.D.(C_{vag} - C_{tiss});$$

where k is a constant, D is the diffusion constant for the molecule, $C_{vag}$ is the molecular concentration in the vagina at the surface of the mucosa and $C_{tiss}$ is the molecular concentration in the tissue surrounding the vagina.

Hence, if $C_{vag}$ drops due to absorption into an intra-vaginal device or due to the flushing away of pharmaceutical agent with vaginal fluids, then the net diffusion of molecules of the pharmaceutical agent across the vaginal mucosa will also fall. Therefore, in order to achieve maximum rates of uptake of pharmaceuticals from the vaginal cavity across the vaginal mucosa and into the surrounding tissues and body fluids, $C_{vag}$ should be maintained at as high a level as possible.

Conventional intra-vaginal devices do not achieve this result. For example, U.S. Pat. No. 5,299,581 attempts to get around this problem by using an intra-vaginal device having a sheet-like cover which is impervious to vaginal fluid. The device comprises a means to expel a medicament once the device has been inserted into the vagina. There is also a means to restrict the escape of excess fluid from the vagina, which in a preferred embodiment is in the form of a sponge or leaf tampon at the lower end of the device. These devices thus reduce absorption of the medicament into the device core to some extent. However, a requirement of this device is that medicaments must be in a liquid form. Such devices are thus not suitable for the sustained release of pharmaceuticals. Furthermore, after insertion of the device, the medicament must be actively introduced into the vagina through a tube within the device. This is cumbersome and inconvenient for the user. Additionally, although the devices are adapted to absorb excess fluid, they are unsuitable for use during menstruation in place of a conventional absorbent article.

The nasal and rectal mucosa also provide a useful anatomical site for systemic drug delivery. The nasal tissue is highly vascularized, providing an attractive site for rapid and efficient systemic absorption. The adult nasal cavity has a capacity of around 20 ml, with a large surface area (approximately 180 $cm^2$) for drug absorption afforded by the microvilli present along the pseudostratified columnar epithelial cells of the nasal mucosa. For non-peptide small molecular compounds, intranasal bioavailability has been shown to be comparable to that of injections. The nasal mucosa has been shown to be amenable to the systemic absorption of certain peptides, as well as to nonpeptide drug molecules. The nasal route is advantageous for nonpeptide drugs that are poorly absorbed orally. One additional advantage to nasal absorption is that it avoids first-pass metabolism by the liver.

The nasal route also offers advantages when rapid and regulated uptake of pharmaceutical is required, such as in the control of acute inflammation, acute respiratory disturbance, emesis, migraine and acute cardiological events.

The present invention aims to provide improved devices for the administration of pharmaceutical agents through the vaginal, nasal or rectal walls. In particular, the present invention aims to provide a simple to use and comfortable device, which provides enhanced uptake of pharmaceutical and which may be employed irrespective of local conditions within the vagina, rectum or nasal cavity.

According to the present invention there is provided a device adapted for insertion into the vagina, rectum or nasal cavity, said device comprising a body, a layer of fluid-impermeable material on at least part of said body and one or more pharmaceutical agents disposed on the surface of said material remote from said body. Preferably, said body comprises an absorbent material.

The fluid-impermeable material forms a layer between the pharmaceutical agent and the body of the device. This layer prevents direct diffusion of the pharmaceutical agent into the device itself, therefore maintaining a high concentration of pharmaceutical agent in the vicinity of the tissue wall and increasing the net diffusion of the pharmaceutical across the mucosa. The presence of the fluid-impermeable layer reduces the inverse dependence of the uptake of the drug on the movement of fluid into and through the vaginal, rectal or nasal cavity. In the case of the intra-vaginal device of the invention, this fluid impermeable layer allows enhanced pharmaceutical uptake to be maintained during menstruation, irrespective of the volume of menstrual flow.

The fluid-impermeable layer should be an inert material, which is thus safe for internal use. The layer should be sufficiently flexible and strong to be suitable for the convenient manufacture of the device. Examples of particularly suitable materials are polyethylene, polypropylene, polyesters, polyolefins, rubbers including polybutadiene and butadiene-styrene rubbers and siliconised materials.

By "fluid-impermeable" is meant herein a material that prevents a substantial amount of normal intra-vaginal, intra-rectal or intra-nasal fluids from penetrating the material during the period of use of the device. The fluid-impermeable layer should preferably have physical characteristics such that it restricts the movement of fluid across the layer to less than 10 microlitres per square centimeter per minute (10 $\mu$L/sq.cm./min) at STP (standard temperature and pressure), more preferably, below 5 $\mu$L /sq.cm./min. During the period of use of the device, preferably less than 5%, more preferably less than 2%, even more preferably less than 1% of the pharmaceutical agent will permeate through the fluid-impermeable layer into the body of the device.

The thickness of the fluid-impermeable barrier is preferably at least 10 $\mu$m, preferably 20 $\mu$m to 2 mm, more preferably 50 $\mu$m to 100 $\mu$m depending on the strength and impermeability of the fluid-impermeable material that is used. For example, for stronger materials, a thinner layer may be acceptable. Importantly, throughout the time period that a device is inserted inside the orifice, the effective permeability characteristic should not be less than the properties of permeability described above. Each type of device (intra-vaginal, intra-nasal and intra-rectal) will have a specified maximum insertion time that will be detailed in a data-sheet that accompanies the product.

The fluid-impermeable layer and the pharmaceutical agents may be combined prior to their attachment to the body of the device. Alternatively, the fluid-impermeable layer may be attached to the body of the device in a first stage and the pharmaceutical agents may be attached to the fluid-impermeable layer in a second stage. Preferably, one or more patches of the fluid-impermeable material are attached to the surface of the body of the intra-device. In this case, the pharmaceutical agents should be applied to the device in aliquots that are coincident with the positions of the patches. Preferably, the fluid-impermeable layer does not completely encapsulate the pharmaceutical agent.

The shape of these patches may be regular or irregular. Conveniently, the patches of fluid-impermeable material are in the form of rectangles, circles, squares, triangles, ellipses or circumferential rings. Where there is more than one patch, the patches may have the same or different dimensions.

A number of different methods may be used to attach the pharmaceutical and fluid-impermeable layer to the body of the device; the particular method used will depend on the size of device, the amount of pharmaceutical and shape and disposition of the active ingredient.

One approach will be to use simple physical methods to achieve attachment. In this embodiment, the fluid-impermeable material will be 'spotted' onto or sprayed onto the device. The material may or may not be freeze-dried prior to the addition of pharmaceutical. Alternatively, the fluid-impermeable layer or the fluid-impermeable layer and the pharmaceutical agent layer may be attached to the device by methods including, for example, heat-sealing, gluing, stitching and needle-punching. The fluid-impermeable layer may be applied to the device in the form of a film or in the form of a liquid that subsequently becomes a film.

In order to coat the pharmaceutical agent onto the surface of the fluid-impermeable layer, any conventional process used in the manufacture of pharmaceutical formulations, for example tablets, may be used. Again, the particular method used will depend on the pharmaceutical in question and the size and disposition of the aliquots.

One method will be compression manufacturing, using, in addition to the pharmaceutical agent, various acceptable anti-adherants, glidants, disintegrating and lubricating agents. Direct compression, wet granulation or dry granulation are distinct methods of the manufacturing process.

Preferably, the pharmaceutical agent may be bonded to the device using an adhesive that functions as the fluid-impermeable layer in addition to binding the pharmaceutical agent. Where the adhesive functions as the fluid-impermeable layer the preferred thickness of the fluid-impermeable layer is 50 $\mu$m to 250 $\mu$m. During the application of the fluid-impermeable adhesive layer and the pharmaceutical agent to the device, some of the pharmaceutical agent may mix into the adhesive in the region of the interface between the pharmaceutical agent and the fluid-impermeable adhesive layer. In this event, the portion of pharmaceutical agent mixed into the fluid-impermeable adhesive is not considered to be included in the amount of pharmaceutical agent available for delivery as this portion of pharmaceutical agent is unable to leave the fluid-impermeable adhesive layer.

The combination of pharmaceutical and fluid-impermeable layer may be further attached to one or more "tethering" components that enable convenient placement of this combined structure within or on the body of the device. This tether is purely for the purpose of fabrication and fulfils no pharmaceutical function. The tether may pass a small distance into the body of the device or alternatively can span one axis of the device. The fluid-impermeable layer should remain substantially intact and remain attached to the body of the device throughout the period of use and removal of the device.

The body of the device may comprise absorbent or non-absorbent material. In the case of an intra-vaginal device, the body preferably comprises absorbent material. The absorbent material may be a cellulose or cellulose derivative fibre, cotton, starch, rayon, sponge, woodpulp, polyolefin, polyester, polyamide, polyurethane, cross-linked carboxymethylcellulose, acrylic acid, methacrylic acid, 2-acrylamido-2-methyl propane sulphonic acid or any mixture of the above. An alternative material can be derived from the formation of hydrogels by polymerization of agents such as unsaturated acid-containing monomers. It should be recognized that some materials are inherently absorbent while in other cases it is the mass of fibres rather than the individual fibre which is absorbent. The addition of surfactants to the surface of fibres can considerably enhance absorbent properties. Suitable surfactants could be anionic or non-ionic in nature.

For the intra-vaginal device, the presence of absorbent material allows the device to fulfil the function of a conventional tampon in addition to its role in delivering pharmaceutical agents. Accordingly, it may be used during menstruation in place of a conventional absorbent article. Such a device may comprise essentially a normal tampon modified to include the fluid-impermeable material and the pharmaceutical agent.

In order to perform the dual function of delivery of pharmaceutical agent and absorption of bodily fluid, the body of the device preferably has an absorbency between 0.6 and 1.35 ml per $cm^3$ of the body of the device, more preferably between 0.75 and 1.2 ml per $cm^3$ of the body of the device. The absorbency of the device may be measured by applying water to one end of a suspended device and determining the maximum uptake of fluid without leakage. As such, the absorbency may be defined as the volume of water that can be applied at room temperature at a rate of 1 ml per 10 seconds.

During menstruation, such a device may thus be used to deliver the pharmaceutical agent and to function simultaneously as a conventional absorbent article. Where the device is intended for use on days on which there is menstruation, or where the onset of menstruation is anticipated, a pharmaceutical agent formulated for more immediate release and uptake through the vaginal mucosa, for example in the form of a dry powder, may be used. Fast delivery of the complete dosage of pharmaceutical agent is preferable in order that the device may be replaced after the recommended period for replacement of such articles, which is generally between 4 and 8 hours. Furthermore, if menstrual flow is particularly heavy and, for example in order to prevent leakage of menses, it becomes necessary to replace the device sooner than expected, then it is essential that complete delivery of the pharmaceutical agent will have occurred prior to removal of the device. In this manner, delivery of an incorrect dosage will be avoided.

A plurality of absorbent articles is expected to be used during any one day while menstruation occurs. Use of the devices of the present invention may be complemented by use of conventional absorbent products. For example, three devices of the present invention may be used alternately with conventional absorbent articles during a period of 24 hours.

Where the body of the intra-vaginal device comprises absorbent material, the proportion of the surface area of the device on which the fluid-impermeable material is located should be from 1% to 50%, preferably from 2% to 30%, more preferably from 3% to 15% of the total surface area of the device. Undesirable responses of vaginal wall tissue to irritant pharmaceutical agents may be reduced by spreading a smaller amount of the agent over a larger number of sites on the device, thereby reducing the exposure of any one point on the vaginal wall to the agent.

Preferably, the device is shaped in such a way that on insertion into the vaginal, rectal or nasal cavity, the physical interaction between the pharmaceutical agent and the mucosal tissue is maximised. In addition, the shape of the device should cause minimal discomfort to the wearer. As the skilled reader will appreciate, the intra-vaginal or intra-rectal device may also be substantially cylindrical, substantially spherical or substantially ellipsoid. The intra-nasal device of the invention should be in the form of a hollow tube adapted for insertion into a nostril. In this manner, the pharmaceutical agent may be delivered, while still allowing the patient to breathe comfortably.

According to an alternative embodiment of the invention, the device of the invention does not comprise an absorbent material.

If desired, the fluid-impermeable material may cover an area of the surface of the device which is larger than the area occupied by the pharmaceutical agent that is applied to the material. In this manner, it will be ensured that the agent is not applied directly to the body of the device even if there are slight errors of positioning during the manufacturing process. Furthermore, if any pharmaceutical agent diffuses laterally, that is along the surface of the material, then the amount of pharmaceutical agent absorbed into the body of the device will be reduced.

The fluid-impermeable layer may be embedded in the body of the device such that the surface of the fluid-impermeable layer lies substantially in the same plane as the remaining surface of the body of the device. In this manner, the device will have a smoother feel and may be more comfortable for the wearer.

The cross-section of the aliquots of pharmaceutical agent may be uniform or non-uniform. Where the cross-section is non-uniform, the cross-sectional shape is preferably bevelled such that the layer of pharmaceutical agent is greatest at the centre of the aliquot.

In one particularly preferred embodiment of the invention, at least one aliquot of pharmaceutical agent is provided as a circumferential ring around the device. Conveniently there are between 1 and 20 rings around the device, preferably between 2 and 5 rings. The ring(s) may be around the long or the short axis of the body of the device, although rings may more easily be applied around the short axis. Where there is more than one ring, the rings may have the same or different dimensions.

The pharmaceutical agent may be applied to the device in any convenient form, such as, for example, in the form of a dry powder or in the form of a sustained release composition. Conveniently, the intra-vaginal device for use on non-menstruation days comprises pharmaceutical agent in a sustained-release formulation. The device may thus be worn for an extended period of time of up to 12 hours, preferably up to 8 hours, avoiding the need for regular replacement.

The pharmaceutical may be formulated with pharmaceutically-acceptable buffers and excipients. Preferably, pharmaceuticals will be low molecular weight entities with molecular weights less than 1,500 Daltons but ideally below 700 Daltons. Pharmaceutical agents may also be peptides or proteins with biological activity. Furthermore, the pharmaceutical agent may be formulated with a penetration enhancer. The excipients used in the formulation of the pharmaceutical layer may remain essentially unaltered during the period of use of the device. Alternatively, the excipients may dissolve and/or diffuse away from the layer of pharmaceutical agent.

The total amount of pharmaceutical contained on the surface of each device will vary depending on the activity of the agent and the eventual tissue concentration to be attained. Generally, the amount will be between 100 µg to 1 g, preferably between 100 µg and 10 mg. The amount selected will depend, of course, on the dosage prescribed, but undesirably high dosages may be avoided using the device of the invention as the concentration in the vicinity of the tissue wall is maintained at a high level due to the structure of the device.

The device may be used in therapy. For example, the device may be used to deliver pharmaceuticals for the treatment of a range of clinical conditions, including, but not limited, to cardiovascular disease, respiratory disease, infective disease, metabolic disease, diseases of the central and peripheral nervous system, diseases of the urogenital tract, psychiatric conditions, gastrointestinal disorders, disorders of the special senses, endocrinological disorders, muscoskeletal disorders and any disease that can be treated by drugs administered via other routes including oral, intravenous, intramuscular, subcutaneous and some topical routes. In a preferred embodiment of the invention, pharmaceuticals delivered using the present invention may be anti-inflammatories and haemostasis-modifying agents.

The device of the present invention may also be used for the delivery of pharmaceutical agents for the treatment of multiple symptoms. This may be achieved by the administration of more than one class of pharmaceutical agent using separate devices inserted within a short time of one another and where the time interval is not less than ten minutes. Alternatively the device may be manufactured such that one device comprises more than one pharmaceutical agent. One particularly preferred combination of pharmaceutical agents for delivery using the intra-vaginal device of the present invention is the combination of an anti-inflammatory prostaglandin synthesis inhibitor and a fibrinolytic inhibitor.

For the intra-vaginal device, the pharmaceutical agent may be one for use in the management of female-specific disorders, for example in conditions associated with the menstrual cycle including dysmenorrhea, endometriosis, fibroids and heavy menstrual bleeding.

Pharmaceuticals that act systemically may also be administered with the intra-vaginal device of the present invention. The intra-vaginal device of the present invention may also be used to deliver other agents through the vaginal mucosa, such as dietary supplements, including vitamins and metal ions, which may be difficult or inconvenient to administer via other routes.

In this embodiment, the pharmaceutical agent may be a steroid, preferably a sex steroid, glucocorticoid or mineralocorticoid. The oestrogenic and prostagenic steroids can bring about a number of therapeutic benefits for clinical syndromes associated with the female cycle. The device of the present invention is suitable for delivery of such steroids when the treatment period is not continuous. Thus steroids can be administered using the device for up to a maximum of six days each month.

The pharmaceutical agent used according to the intra-vaginal device of the present invention may modulate thrombotic and fibrinolytic cascades and thus control the abnormal bleeding that may occur during menstruation. Pharmaceutical agents that inhibit fibrinolysis when taken orally are known to be effective in the control of menstrual bleeding. These fibrinolytic inhibitors work by inhibiting the breakdown of blood clots in the spiral arteries and arterioles. Fibrinolytic inhibitors have been reported to decrease blood loss by up to 50% and their efficacy is greatest in those patients with heavy blood loss. However, there is concern that oral administration of anti-fibrinolytic agents might be associated with systemic thrombotic complications. In particular, to achieve a therapeutically useful systemic concentration through oral administration, it is usually necessary to administer high levels of the pharmaceutical agent and these high levels may cause side effects. In contrast, the device of the present invention enables the pharmaceutical agent to be administered close to the treatment site, thus lowering the systemic concentration and reducing the occurrence of unwanted side-effects.

Anti-fibrinolytic agents suitable for administration using the device of the present invention include tranexamic acid, acexamic acid, aminocaproic acid, aprotinin and ethamsylate. Certain biologically active peptides and proteins, for example the snake venom enzyme Batroxobin, may also be used.

Other preferred pharmaceutical agents for delivery using this aspect of the present invention include anti-inflammatory agents, that are known to reduce the symptoms associated with painful menstruation. Such agents may be steroidal or non-steroidal. Examples of non-steroidal anti-inflammatory agents (NSAIDs) include prostaglandin synthesis inhibitors and prostaglandin receptor antagonists, and in addition to providing pain relief may also alter blood clotting. NSAIDs may be used in the treatment of Dysfunctional Uterine Bleeding (DUB) and in the treatment of dysmenorrhoea.

One other preferred class of anti-inflammatories for use in the device of the present invention are cyclo-oxygenase inhibitors, for example acetylsalicylic acid, salicylsalicylic acid, salicylic acid, trilisate, disalcid and salts thereof.

Further preferred anti-inflammatory pharmaceutical agents include diclofenac, flurbiprophen naproxen, piroxicam, mefenamic acid, indomethacin, sulindac, meclofenamate, diflunisal, tolmetin, acetominophen, ibuprofen, oxaprozin, etodolac, fenoprofen, ketoprofen and nabumetone.

Tocolytics form another class of pharmaceutical agents useful for delivery using the device of this aspect of the invention. This class of compounds relax the muscle wall of the uterus and may relieve painful menstruation and may be used in the treatment of "cramps" associated with menstruation. Tocolytics include anti-muscarinic pharmaceutical agents and $\beta_2$-agonists. Preferred anti-muscarinic agents include atropine sulphate (or its other salts), benztropin mesylate, biperiden lactate (or its other salts), cyclopentolate hydrochloride, dicyclomine hydrochloride, enepromium salts, glycopyrronium bromide, homatropin methobromide, hyoscine butylbromide (or its other salts), ipratropium bromide, propantheline bromide, alverine citrate or mebeverine hydrochloride. Preferred $\beta_2$-agonists include short-acting agents, such as ritrodine, orciprenaline, salbutamol, terbutaline, and long-acting selective agents, such as salmeterol or formoterol. Other pharmaceutical agents which have a tocolytic effect, and which may be delivered using the device of the present invention, include aminophylline, which brings about a tocolytic effect by inhibiting the enzyme phosphodiesterase, and calcium antagonists such as nifedipine.

The intra-rectal device and the intra-nasal device may comprise any of the above-mentioned pharmaceutical agents. In addition, further pharmaceutical agents useful for delivery using the intra-rectal or intra-nasal device include adrenaline, sodium nitroprusside, an anti-emetic, such as ondansetron, an anti-migraine, such as sumatriptan, a bronchodilator such as salbutamol or theophylline, or a diuretic such as frusemide.

Any of the above-mentioned pharmaceutical agents may be in the form of a mixture of optical isomers. Alternatively, the pharmaceutical agent may be enantiomerically pure. Furthermore, as and when new pharmaceutical agents are developed these will also be suitable for incorporation into the device of this invention.

In use, the device of the invention is inserted into the vaginal, rectal or nasal cavity where it is retained for a period of time between 30 minutes and 12 hours, preferably between 4 and 8 hours. During this period, the surface of the device remains in a position, contacting the vaginal wall. Molecules of the pharmaceutical agent diffuse through the mucosal tissue into the underlying tissues, blood and lymph. The device of the invention may be used in a method of treating a disease in a patient, comprising administering a pharmaceutical agent to the patient using the device.

The intra-vaginal device may be used at any stage of the menstrual cycle. The intra-vaginal devices of the present invention may be used intermittently or cyclically.

Generally, the device according to the invention comprises withdrawal means. For example, in the case of the intra-vaginal or intra-rectal device, the withdrawal means is a string attached to the device that may be pulled to remove the device from the vagina or rectum.

The device may also comprise insertion means. Preferably the insertion means comprises a first hollow cylindrical tube defining a cartridge for receiving said device and a second hollow cylindrical plunger slidably received within said first cylindrical tube.

The device may be contained in a sterile package prior to use. A number of sterile packages containing separate devices may be packaged together, for example in a box. A pharmacist might dispense to a patient a box containing a plurality of sterile packages comprising the device of the present invention for a course of prescription.

Specific embodiments of the present invention are now described, by way of example only, with reference to the accompanying drawings in which:

FIG. 6 shows a sectional view of a substantially cylindrical intra-vaginal or intra-rectal device comprising one pharmaceutical-containing ring, which is embedded in the body of the device.

FIG. 7 shows a side view of a substantially cylindrical intra-vaginal or intra-rectal device comprising a plurality of pharmaceutical-containing rings.

FIG. 8 shows a sectional view taken along the line D—D of the intra-vaginal or intra-rectal device of FIG. 7.

FIG. 9 shows a side view of a substantially cylindrical intra-vaginal or intra-rectal device comprising a plurality of circular patches of fluid-impermeable layer and pharmaceutical agent.

FIG. 10 shows a cross-sectional view of an intra-vaginal or intra-rectal device in which the layer of fluid-impermeable material and pharmaceutical agent are attached to a tether positioned within the body of the device.

FIG. 11 shows an intra-nasal device.

Figure 1:
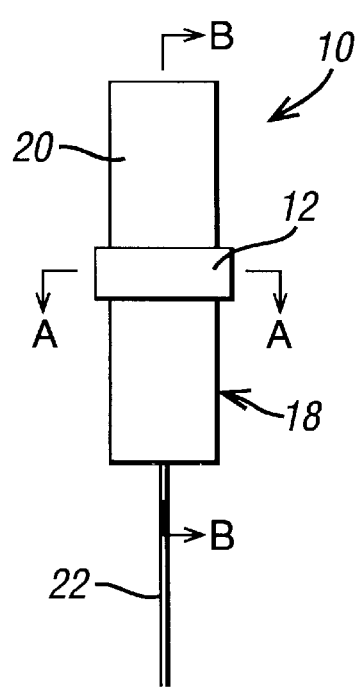
FIG. 1 shows a side view of a substantially cylindrical intra-vaginal or intra-rectal device comprising one pharmaceutical-containing ring.
Figure 2:
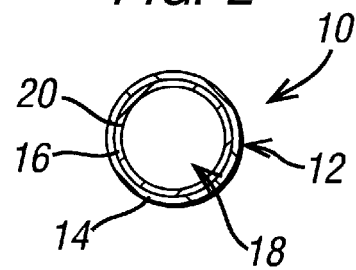
FIG. 2 shows a sectional view taken along the line A—A of the intra-vaginal or intra-rectal device of FIG. 1.
Figure 3:
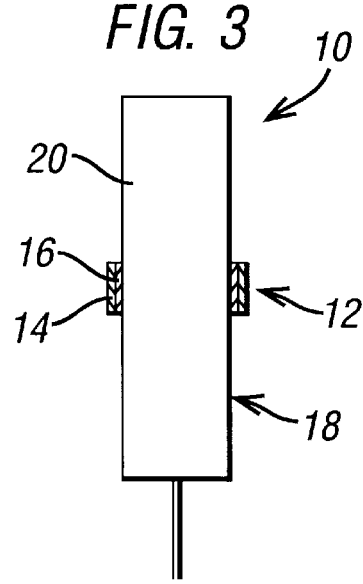
FIG. 3 shows a sectional view taken along the line B—B of the intra-vaginal or intra-rectal device of FIG. 1.

With reference to FIGS. 1 to 3, one embodiment of the present invention is an intra-vaginal or intra-rectal device (10) in the form of a substantially cylindrical tampon. The device (10) comprises a body (18), which may be made of an absorbent material. A fluid-impermeable layer (16) is attached to the surface (20) of the body (18). The fluid-impermeable layer (16) forms a ring around the circumference of the body (18). A formulation of pharmaceutical agent (14) is disposed on the layer of fluid impermeable material (16). The combination of the fluid-impermeable barrier and pharmaceutical layer forms a circumferential ring (12) around the core (18). The fluid-impermeable layer and the pharmaceutical may be combined prior to their attachment to the core (18) or the fluid-impermeable layer may be attached to the core in a first stage and the pharmaceutical may be attached to the fluid-impermeable layer in a second stage. A string (22) is attached to the body of the device (10) to aid withdrawal of the device after use.

Figure 4:
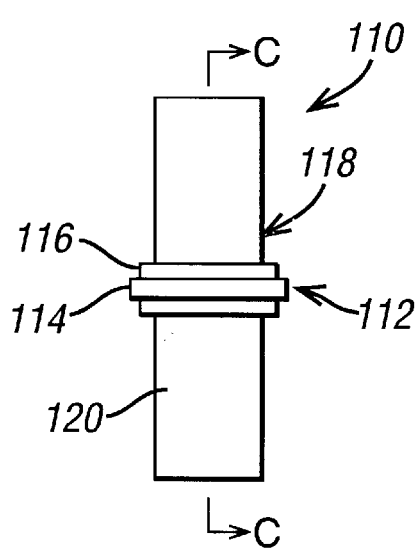
FIG. 4 shows a side view of a substantially cylindrical intra-vaginal or intra-rectal device comprising a pharmaceutical-containing ring, which is separated from the interior of the device by a wider ring of a fluid-impermeable layer.
Figure 5:
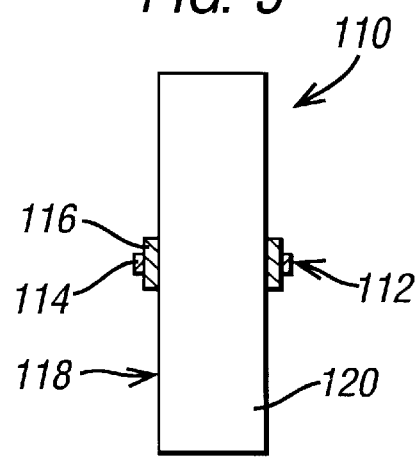
FIG. 5 shows a sectional view taken along the line C—C of the device of FIG. 4.

With reference to FIGS. 4 and 5, a second embodiment of the present invention provides an intra-vaginal or intra-rectal device (110) in which the circumferential ring of pharmaceutical agent (114) is narrower than the ring of fluid-impermeable material (116).

With reference to FIG. 6, another embodiment of the present invention provides an intra-vaginal or intra-rectal device (210) in which a circumferential ring (212) is embedded in the device such that the surface of the circumferential ring (212) lies substantially in the same plane as the surface (220) of the body of the device.

FIGS. 7 and 8 show another embodiment of the present invention in which a plurality of circumferential rings (312) are attached to the surface (320) of the body (318) of the device. Each circumferential ring (312) comprises a fluid-impermeable layer (316) attached to the surface (320) and a layer of pharmaceutical agent (314) attached to the fluid-impermeable layer (316).

The combination of the pharmaceutical and fluid-impermeable barrier may adopt a variety of shapes on the surface of the intra-vaginal or intra-rectal devices of the present invention. In FIG. 9, the device of the invention has a plurality of circular patches (412). Each circular patch comprises a fluid-impermeable layer (416) attached to the surface (420) and a layer of pharmaceutical agent (414) attached to the fluid-impermeable layer (416).

One or more tethers may be used within the device to facilitate and strengthen the attachment of pharmaceutical agent and fluid-impermeable layer to the body of the device. FIG. 10 shows an intra-vaginal or intra-rectal device in which tethers (521) are positioned within the body of the device. The fluid-impermeable layers are attached to the tethers, so strengthening their linkage with the body of the device.

With reference to FIG. 11, a further embodiment of the invention is an intra-nasal device (610) in the form of a substantially cylindrical hollow tube. The device comprises a body (618), which may be made of an absorbent material. A fluid-impermeable layer (616) is attached to the surface (620) of the body (618). The fluid-impermeable layer (616) forms a ring around the circumference of the body (618). A formulation of pharmaceutical agent (614) is disposed on the layer of fluid impermeable material (616). The combination of the fluid-impermeable barrier and pharmaceutical layer forms a circumferential ring (612) around the core (618).

Figure 12:
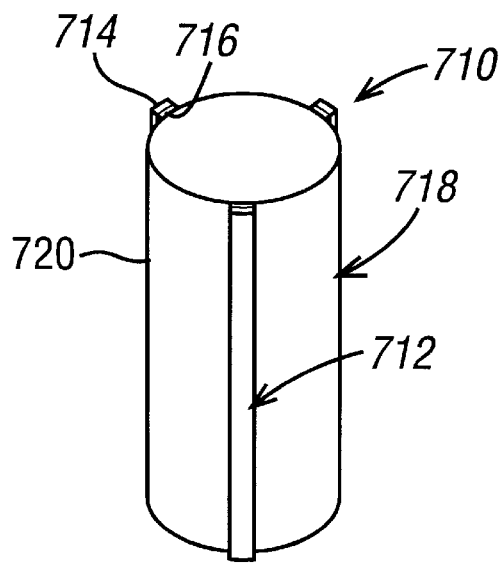
FIG. 12 shows a side view of a substantially cylindrical intra-vaginal or intra-rectal device comprising a plurality of pharmaceutical-containing longitudinal strips.

With reference to FIG. 12, a further embodiment of the present invention provides an intra-vaginal or intra-rectal device (710) in which a plurality of strips (712) are attached to the surface (720) of the body (718) of the device. The strips are substantially aligned along the longitudinal axis of the device. Each strip comprises a fluid-impermeable layer (716) attached to the surface (720) and a layer of pharmaceutical agent (714) attached to the fluid-impermeable layer (716). When, in use, the body (718) of the device (710) absorbs fluid the strips (712) do not restrict the expansion of the device.

Figure 13:
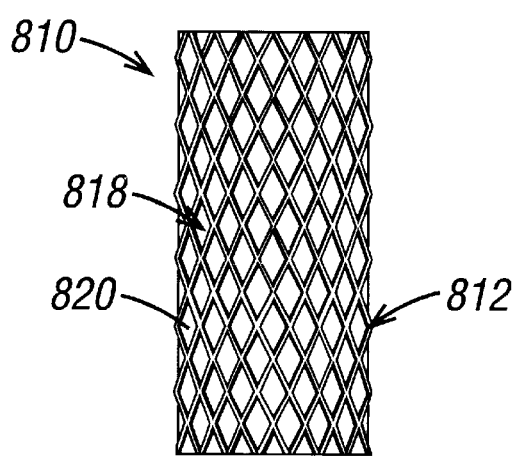
FIG. 13 shows a side view of a substantially cylindrical intra-vaginal or intra-rectal device comprising a pharmaceutical-containing lattice prior to absorption of fluid.
Figure 14:
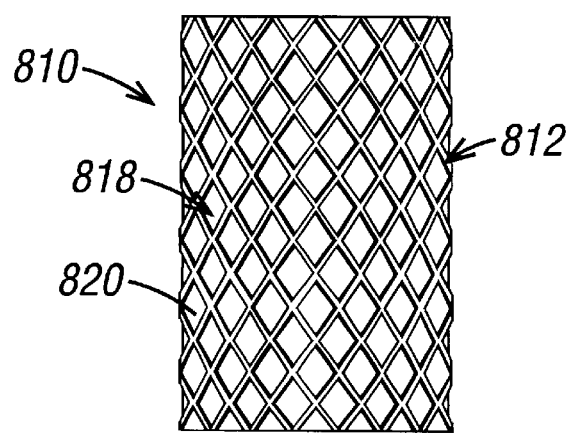
FIG. 14 shows a side view of the intra-vaginal or intra-rectal device of FIG. 13 following absorption of fluid by the body of the device.

With reference to FIGS. 13 and 14, a further embodiment of the present invention provides an intra-vaginal or intra-rectal device (810) in which a lattice (812) is attached to the surface (820) of the body (818) of the device. The lattice comprises a fluid-impermeable layer attached to the surface (820) and a layer of pharmaceutical agent attached to the fluid-impermeable layer. In-use, the body of the device (818) may absorb fluid, causing the device to swell. Consequently, the lattice (812) stretches from the configuration shown in FIG. 13 to the configuration shown in FIG. 14. In this way, the lattice (812) allows the device to expand freely. Moreover, as the device swells and the lattice stretches, the position of the pharmaceutical agent in the lattice is inevitably moved with respect to the wall of the body cavity in which the device resides, thereby reducing exposure of the pharmaceutical agent to any one part of the mucosal surface.

EXAMPLE 1

A layer of methacrylate polymer, obtained from commercially available adhesives, was formed on the surface of three commercially available tampons by applying thin layers of unpolymerized material to small areas of the tampon surface and allowing the layers to set hard in an oven at 120° C.

About 20 $\mu$l of silver nitrate solution was applied to the surface of the polymer layers of each tampon. As a comparison, 20 $\mu$l of silver nitrate solution was applied to an area of the tampons where the surface was not coated with a polymer layer. Each tampon was allowed to dry in an oven at 120° C.

Following drying, a tissue and gauze layer that had been soaked in sodium hydroxide was applied to the surface of each tampon. These tissue layers were intended to model the surface of the vaginal mucosa. The ensuing reaction between the silver nitrate and the sodium hydroxide caused insoluble oxides of silver to be deposited on each tissue and gave a visual indication of the amount of silver nitrate that had been available at the surface of each tampon.

Figure 15:
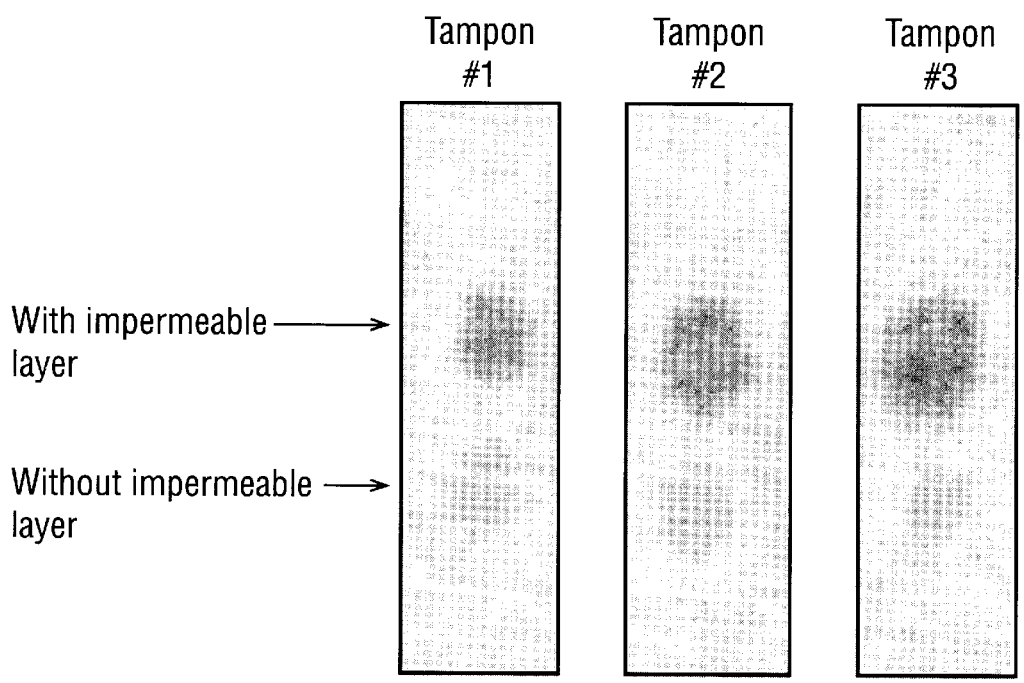
FIG. 15 is a photograph showing the effect of the presence of a fluid-impermeable layer.

FIG. 15 shows a photograph of the tissue layers that were obtained following application to the surface of three separate tampons. The photograph shows that there was more silver nitrate available for reaction with the sodium hydroxide in the tissue in the areas where there was a layer of methacrylate polymer that acted as a fluid-impermeable layer. In contrast, in the areas where there was no methacrylate polymer layer, much of the silver nitrate had been absorbed or diffused into the body of the tampon and was no longer available for reaction with the sodium hydroxide in the tissue. Consequently, the presence of a fluid-impermeable layer increases the concentration of silver nitrate available for reaction.

EXAMPLE 2

Devices according to the present invention were made and used to deliver a pharmaceutical agent intra-vaginally in Rhesus monkeys.

Materials used in the manufacture of commercial tampons for human use were reconstituted to produce tampons with dimensions 7 mm×25 mm or 5 mm×25 mm. Depending on the weight of an individual Rhesus monkey, one of these sizes of tampon was able to be conveniently inserted into the vagina of the Rhesus monkey.

A strip of double-sided adhesive tape was secured to the surface of the tampons to function as the fluid-impermeable layer. Mefenamic acid powder was "dusted" onto the surface of the tape and non-adherent mefenamic acid was removed.

Rhesus monkeys were anaesthetised with ketamine hydrochloride and one of the above-mentioned tampon devices was inserted into the vagina of each monkey. A 19 gauge catheter was inserted into the saphenous vein of each monkey. This catheter was used to collect blood samples during the course of the study. The monkeys were returned to their cages when appropriate.

Figure 16:
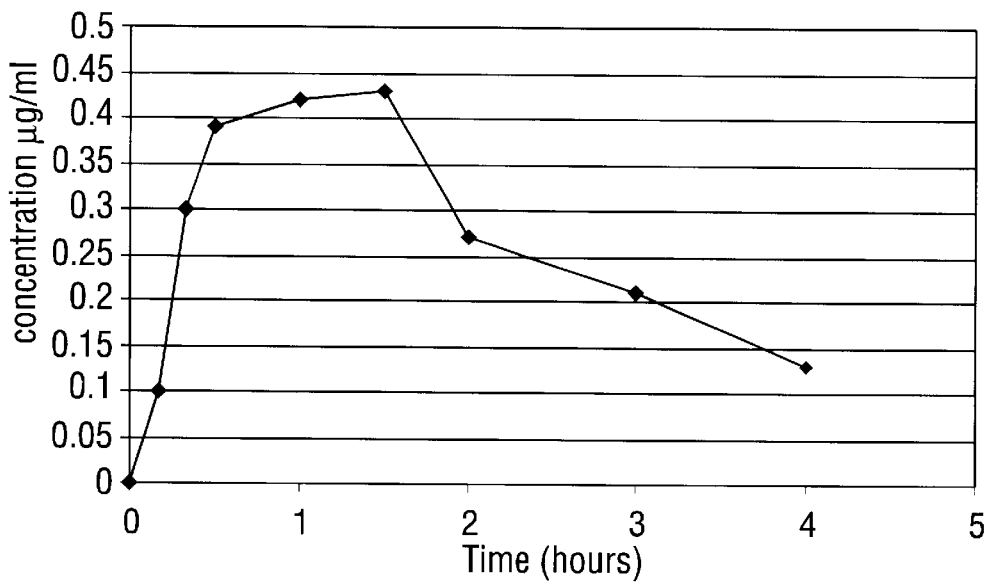
FIG. 16 is a graph showing blood levels of mefenamic acid in Rhesus monkeys after insertion of an intravaginal device of the present invention.

Blood samples were taken at intervals and plasma was prepared and frozen. After the completion of the study, all plasma samples were assayed for the concentration of mefenamic acid. FIG. 16 shows a graph of the concentration in $\mu$g/ml of mefenamic acid found in the plasma of the Rhesus monkeys with time after insertion of the devices of this example. The results show that mefenamic acid was transported across the vaginal mucosa and systemic circulation of mefenamic acid was achieved.

EXAMPLE 3

Further devices according to the present invention were made and used to deliver a pharmaceutical agent intra-vaginally in Rhesus monkeys.

Materials used in the manufacture of commercial tampons for human use were reconstituted to produce tampons with dimensions 7 mm×25 mm or 5 mm×25 mm. Depending on the weight of an individual Rhesus monkey, one of these sizes of tampon was able to be conveniently inserted into the vagina of the Rhesus monkey.

Wax material was used to create a fluid-impermeable layer of the tampons by warming the wax layer to make it adhere to the body of the tampon. Once the wax layer had been applied, mefenamic acid was "dusted" onto the device while the device was warmed to aid adhesion between the wax and the mefenamic acid. Non-adherent mefenamic acid was removed.

Rhesus monkeys were anaesthetised with ketamine hydrochloride and one of the above-mentioned tampon devices was inserted into the vagina of each monkey. A 19 gauge catheter was inserted into the saphenous vein of each monkey. This catheter was used to collect blood samples during the course of the study. The monkeys were returned to their cages when appropriate.

Figure 17:
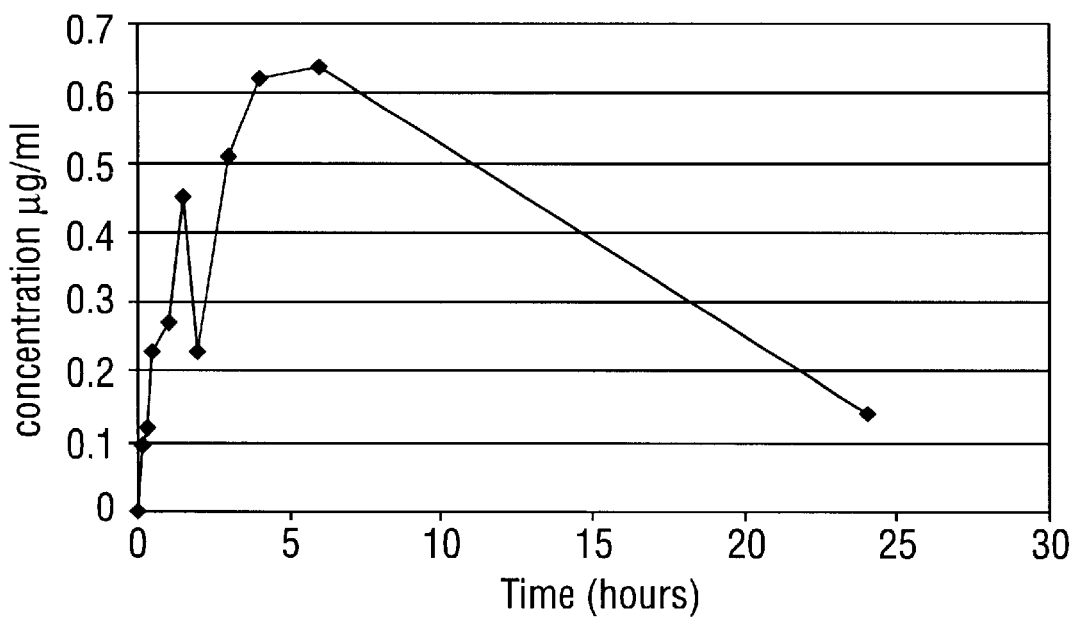
FIG. 17 is a graph showing blood levels of mefenamic acid in Rhesus monkeys after insertion of an intravaginal device of the present invention.

Blood samples were taken at intervals and plasma was prepared and frozen. After the completion of the study, all plasma samples were assayed for the concentration of mefenamic acid. FIG. 17 shows a graph of the concentration in $\mu$g/ml of mefenamic acid found in the plasma of the Rhesus monkeys with time after insertion of the devices of this example. The results show that mefenamic acid was transported across the vaginal mucosa and systemic circulation of mefenamic acid was achieved.

EXAMPLE 4

Eight devices were prepared as described in Example 3. The devices were assayed and the average amount of mefenamic found to be in each device was 6.4 mg. Each device was inserted into the vagina of one of eight Rhesus monkeys. The monkeys all weighed in the range 7.27 kg to 8.95 kg.

Figure 18:
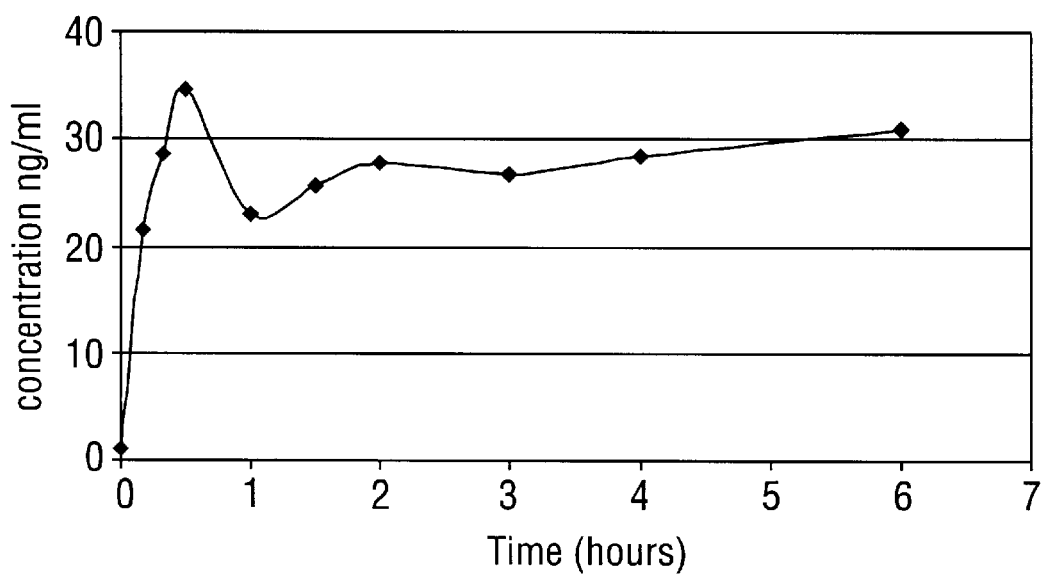
FIG. 18 is a graph showing blood levels of mefenamic acid in Rhesus monkeys after insertion of an intravaginal device of the present invention.

Blood samples were taken from the Rhesus monkeys and the samples were assayed as described in Example 3, at the time intervals shown in the graph of FIG. 18. The results of this study are shown in the graph of FIG. 18, which indicates the concentration in ng/ml of mefenamic acid found in the plasma of the Rhesus monkeys with time following insertion of the devices of this example. Each point of the graph of FIG. 18 represents the mean value of the concentration of the eight monkeys. The results show that mefenamic acid was transported across the vaginal mucosa and systemic circulation of mefenamic acid was achieved.

EXAMPLE 5

A comparison was made between the uptake of mefenamic acid in Rhesus monkeys where the mefenamic acid was introduced intra-vaginally using the devices of Example 3 and the uptake of mefenamic acid in Rhesus monkeys where a slurry comprising mefenamic acid was introduced intra-vaginally.

The slurry of mefenamic acid applied to a Rhesus monkey comprised a total amount of mefenamic acid that was greater than ten times that applied to a Rhesus monkey using the device of Example 3.

Figure 19:
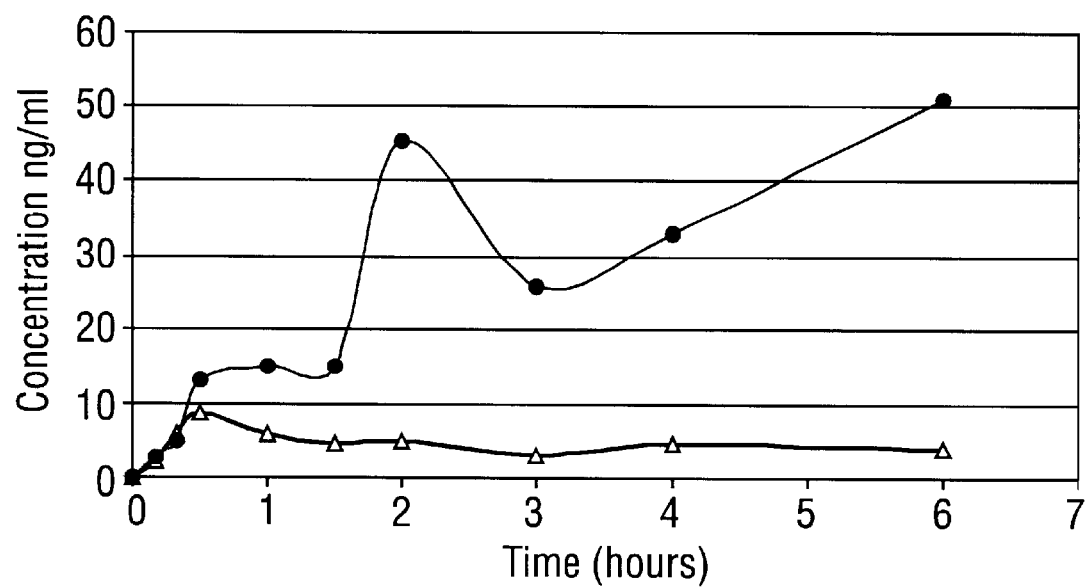
FIG. 19 is a graph showing a comparison between the uptake of mefenamic acid across the vaginal mucosa using a device of the present invention and a slurry comprising mefenamic acid.

Blood samples were taken from the Rhesus monkeys and the samples were assayed as described in Example 3, at the time intervals shown in the graph of FIG. 19. The results of this study are shown in the graph of FIG. 19, which indicates the concentration in ng/ml of mefenamic acid found in the plasma of the Rhesus monkeys with time following insertion of the devices (circles) and slurry (triangles) of this example. The results show that despite the far greater amount of mefenamic acid contained in the slurry inserted into the vagina of the Rhesus monkeys, only limited uptake of mefenamic acid by the monkeys was achieved. In contrast, the use of a device of this invention resulted in the transportation of mefenamic acid across the vaginal mucosa and systemic circulation of mefenamic acid in the Rhesus monkeys was achieved.

It will, of course, be understood that the present invention has been described above purely by way of example and that modifications of detail can be made within the scope of the invention.

What is claimed is:

1. A device adapted for insertion into the vagina, rectum or nasal cavity, said device comprising a body, a layer of fluid-impermeable material attached to at least part of said body and one or more pharmaceutical agents disposed on the surface of said material remote from said body, wherein said body comprises an absorbent material, the fluid-impermeable material is applied to the surface of said device in the form of one or more discrete patches, and wherein said pharmaceutical agent is disposed on the device in aliquots that are coincident in position with said patches of fluid-impermeable material.

2. The device of claim 1, wherein said fluid-impermeable material is any one of polyethylene, polypropylene, a polyester, a polyolefin, a rubber such as a polybutadiene and a butadiene-styrene rubber or siliconised materials.

3. The device of claim 1, wherein said layer of fluid-impermeable material is between 10 $\mu$m and 2 mm in thickness.

4. A method of treating a disease in a patient, comprising administering a pharmaceutical agent to a patient using a device according to claim 1.

5. The device of claim 4, wherein the shape of the patches of said fluid-impermeable material are in the form of circles, rectangles, squares, triangles, ellipses or circumferential rings.

6. The device of claim 4, wherein said fluid impermeable barrier covers a larger area of the surface of the device than does each aliquot of pharmaceutical agent.

7. The device of claim 4, wherein the cross-sectional shape of said aliquots of pharmaceutical are uniform.

8. The device of claim 4, wherein each aliquot of pharmaceutical agent forms a circumferential ring around said device.

9. The device of claim 1, wherein said pharmaceutical agent is in the form of a dry powder.

10. The device of claim 1, wherein said pharmaceutical agent is formulated with one or more pharmaceutically-acceptable excipients.

11. The device of claim 1, wherein said pharmaceutical agent is in the form of a sustained release composition.

12. The device of claim 1, wherein said pharmaceutical agent is an anti-fibrinolytic agent, such as tranexamic acid or aminocaproic acid, an anti-inflammatory agent, such as ibuprophen or mefenamic acid, a tocolytic agent, such as hyoscine or ritrodine, or a combination of anti-fibrinolytic, anti-inflammatory and/or tocolytic agents.

13. The device of claim 1, which is an intra-nasal device or an intra-rectal device, and wherein said pharmaceutical agent is adrenaline, sodium nitroprusside, an anti-emetic, such as ondansetron, an anti-migraine, such as sumatriptan, a bronchodilator such as salbutamol or theophylline, or a diuretic such as frusemide.

14. The device of claim 1, wherein the amount of pharmaceutical agent disposed on the surface is between 10 $\mu$g and 1 g.

15. The device of claim 1, wherein the amount of pharmaceutical agent disposed on the surface is between 100 $\mu$g and 10 mg.

16. The device of claim 1, wherein said absorbent material is cellulose or cellulose derivative fibres, cotton, starch, rayon, sponge, woodpulp, polyolefin, polyester, polyamide, polyurethane, cross-linked carboxymethylcellulose, acrylic acid, methacrylic acid, 2-acrylamido-2-methyl propane sulphonic acid or a mixture thereof, or a hydrogel.

17. The device of claim 1, wherein said device is a tampon.

18. The device of claim 17, wherein the shape of said tampon is substantially cylindrical, substantially spherical or substantially ellipsoid.

19. The device of claim 1, further comprising withdrawal means for removal of the device from the vaginal or rectal cavity.

20. The device of claim 19, wherein said withdrawal means is a string attached to said device.

21. The device of claim 1, further comprising inserting means.

22. The device of claim 21, wherein said inserting means comprises a first hollow cylindrical tube defining a cartridge for receiving said device and a second hollow cylindrical plunger slidably received within said first cylindrical tube.

23. The device of claim 1, which is an intra-nasal device, and wherein said device is hollow.

* * * * *